United States Patent [19]
Grotendorst

[11] Patent Number: 5,097,914
[45] Date of Patent: Mar. 24, 1992

[54] METHOD AND DEVICE FOR PRODUCING UNADULTERATED WATER SAMPLES IN DRILLING A WELL

[75] Inventor: Gerhard Grotendorst, Borken, Fed. Rep. of Germany

[73] Assignee: Terratronic Vertrieb von Zielbohrsystemen GmbH, Munich, Fed. Rep. of Germany

[21] Appl. No.: 526,286

[22] Filed: May 21, 1990

[30] Foreign Application Priority Data

May 23, 1989 [DE] Fed. Rep. of Germany ....... 3916731
Dec. 18, 1989 [DE] Fed. Rep. of Germany ....... 3941763

[51] Int. Cl.$^5$ .......................................... E21B 25/00
[52] U.S. Cl. ...................... 175/59; 175/314; 166/264
[58] Field of Search ............ 175/57, 59, 314; 166/264, 369, 380

[56] References Cited

U.S. PATENT DOCUMENTS

| | | | |
|---|---|---|---|
| 3,902,323 | 9/1975 | Watanabe | 175/314 X |
| 4,315,542 | 2/1982 | Dockins, Jr. | 166/117.7 |
| 4,693,318 | 9/1987 | Petrovic | 166/380 |

FOREIGN PATENT DOCUMENTS

| | | |
|---|---|---|
| 0062022 | 10/1982 | European Pat. Off. . |
| 3309031 | 9/1984 | Fed. Rep. of Germany . |
| 8502093 | 6/1985 | Fed. Rep. of Germany . |

Primary Examiner—William P. Neuder
Attorney, Agent, or Firm—Remy J. VanOphem

[57] ABSTRACT

A method and device is used for producing uncontaminated water samples when drilling a well, using a hollow bar for transporting drilling fluid whose conduits consist of nonperforated tubes and at least one perforated tube; the water sample is pumped through filter sand from a water-conducting horizontal, approached by the boring bar, via a perforated insert positioned in the latter after the filter sand is deposited between the perforated tube, the adjacent nonperforated conduit and the bore wall and incorporated into the system as a filter. The bore up to the first water-conducting horizontal is drilled with the closed perforated insert and the first water sample obtained. After closing the perforations, drilling is continued and the filter sand removed until the next water-conducting horizontal is reached, from which a second water sample is taken after re-opening the perforations.

17 Claims, 3 Drawing Sheets

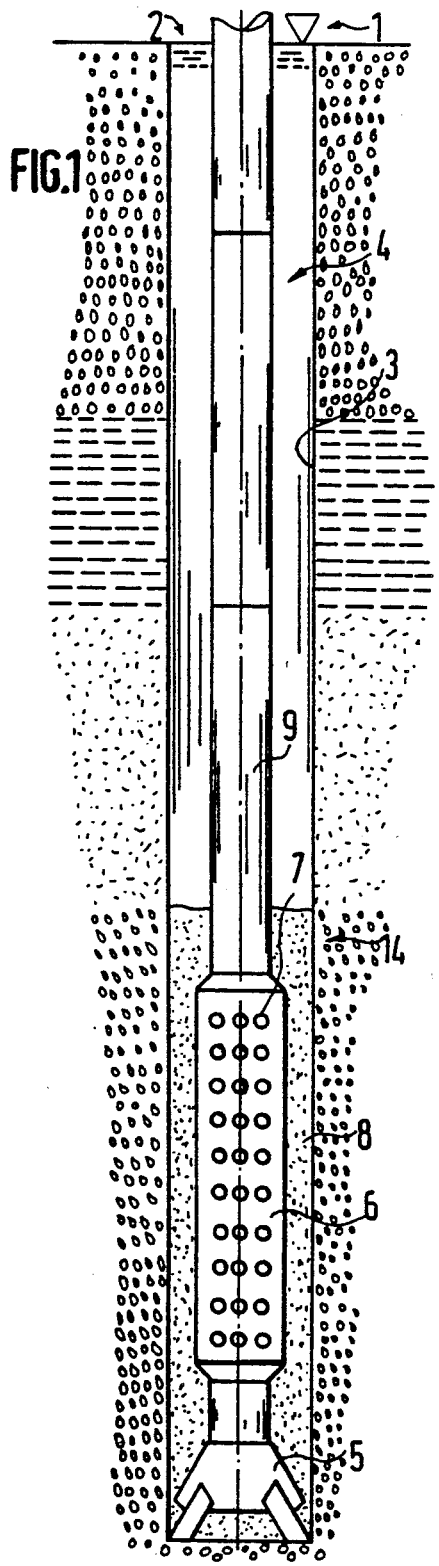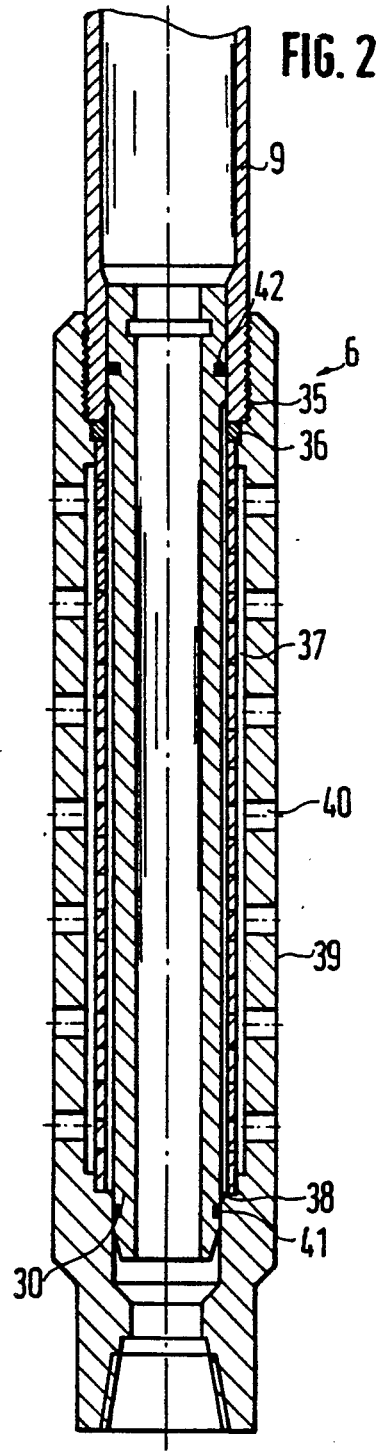

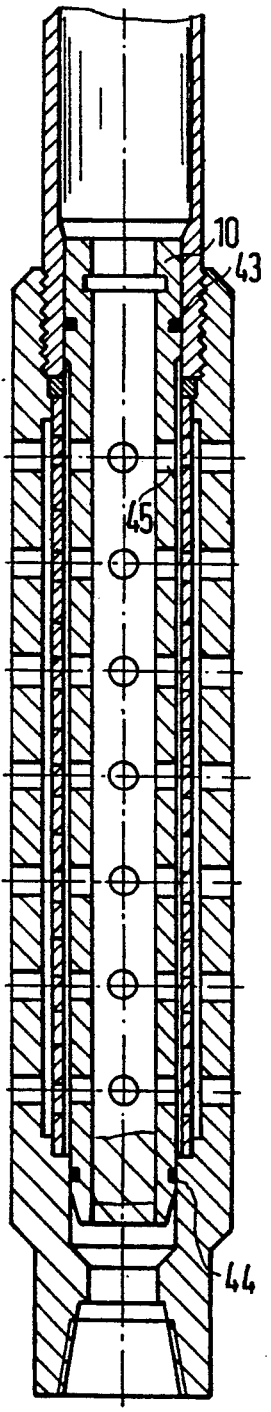
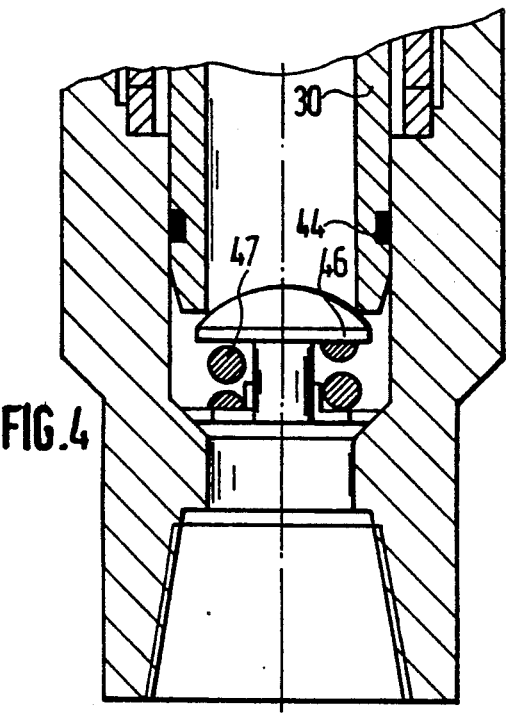
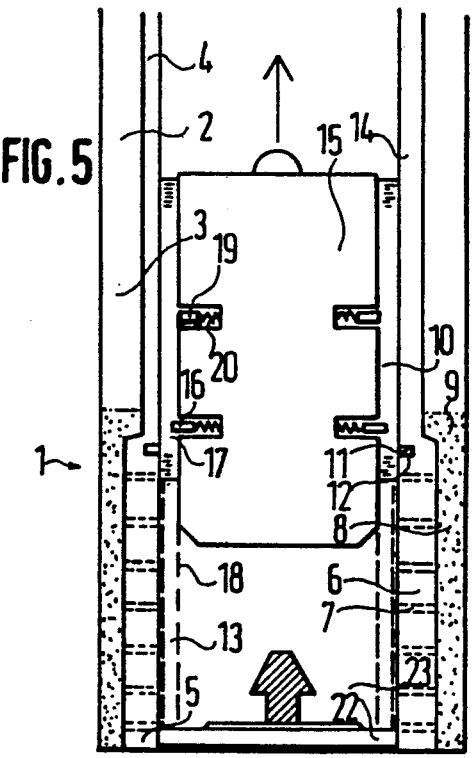

METHOD AND DEVICE FOR PRODUCING UNADULTERATED WATER SAMPLES IN DRILLING A WELL

BACKGROUND OF THE INVENTION

1. Field of the Invention

The invention relates to a production method for producing unadulterated water samples when drilling a well and also relates to a device for implementing the method.

2. Description of the Prior Art

In the method according to the invention, water samples originating in a water-conducting horizontal approached by the bore are taken from contaminated soil. The samples are free of contamination which can enter the water samples by pumping the samples through the hollow bar and the bore as soon as the samples have left the water-conducting horizontal. Such contamination is generally based on elements of the bore rinse which has absorbed stagnant water from the surrounding rock or previously drilled water-conducting horizontals and, therefore, contains adulterating substances such as contamination when drilling in contaminated soil. The method according to the invention makes it possible to suppress such contamination in the sampled water and, therefore, to analyze which water qualities can be expected for which samples.

This is based primarily on the largely ring-shaped filter sand body, through which the water sample is pumped, deposited in the circular space between the boring bar and the bore before each sample is taken. The top section of the sand filter body, which surrounds a nonperforated conduit in the hollow bar, traps solid matter in the rinse and is compressed, forming a natural ring seal against the water-conducting horizontal in which the perforated bar conduit is positioned. In the method according to the invention, the described filter sand body is incorporated into the system after a period of time when pumping the water sample out of the bore, until the above-mentioned ring seal is formed and clear water flows from the approached horizontal. In doing this, the filter sand is restrained by the bar.

The principle of this method is already known from PCT application WO 82/04,352. If several groundwater horizontals lying above one another are to be tested according to this method, the bar has a large number of perforated bar conduits which are positioned according to the distance of the water-conducting layers and are each fitted with a collecting mechanism for closing off the bore wall. These mechanisms are extended when the bar is lifted and restrain the deposited filter sand so that the above-mentioned ring-shaped filter sand bodies can be formed.

This previously known method can normally be implemented with only two bars which must be inserted alternately or sequentially into the bore. The bar necessary for taking samples has a relatively complex structure and requires knowledge of the distance between the water-conducting horizontals in order to arrange the perforated bar conduits at the correct intervals for producing the filter sand bodies. According to this method, the well bore is, in general, partially or fully drilled and the bar containing the perforated bar conduits subsequently inserted. For organizational reasons, this is quite disadvantageous and easily produces incorrect results if one must drill in unknown soil and does not know how deep the bore must be drilled in order to strike a water-conducting horizontal which will supply water of a suitable quality and quantity.

The invention is based on the goal of implementing the previously known method so as to eliminate the need to change the bars between water samples, yet still obtain unadulterated water samples.

SUMMARY OF THE INVENTION

According to the invention, the boring bar itself is used to pump the water samples through the hollow bar conduits, but not to drill the sample bore. Surprisingly, it was established that the ring-shaped filter sand plug described above, which is necessary for obtaining unadulterated water samples, is destroyed by the bore rinse as soon as the perforated bar conduit is closed and drilling continued. This makes it possible to halt the bore in every water-conducting horizontal approached successively from top to bottom as soon as the perforated bar conduit reaches the conducting horizontal and to deposit a filter sand body without the use of a special collecting device, which further simplifies the boring bar.

The advantage of the invention lies in the fact that, according to the proposed method, unadulterated water samples can be obtained as needed during drilling of the well bore without withdrawing the bar. This simplifies and considerably accelerates drilling work. With the method according to the invention, wells whose depths are unknown initially can be drilled until reaching a water-conducting horizontal which supplies water of a suitable quality and quantity. The method according to the invention is, therefore, particularly suitable for use as a testing method for unknown soils whose content of contaminating substances may be unknown.

The details, further characteristics, and other advantages of the invention will become apparent from the follow description of a device for implementing the described method according to the invention taken in conjunction with the appended drawings.

BRIEF DESCRIPTION OF THE DRAWINGS

FIG. 1 shows a schematic and longitudinal partially cross-sectional view of a first embodiment of the invention, omitting all details not necessary to understand the invention;

FIG. 2 shows an enlarged illustration of the perforated bar conduit according to the invention represented in FIG. 1 for drilling the bore;

FIG. 3 shows an illustration of the perforated bar conduit in FIG. 2 for taking water samples;

FIG. 4 shows an enlarged representation of the object of FIG. 3, depicting a detail of the perforated bar conduit;

FIG. 5 shows an alternate embodiment of the invention which is largely equivalent to the representation in FIG. 1, but without the drilling tool;

DETAILED DESCRIPTION OF THE PREFERRED EMBODIMENT

Figure 6:
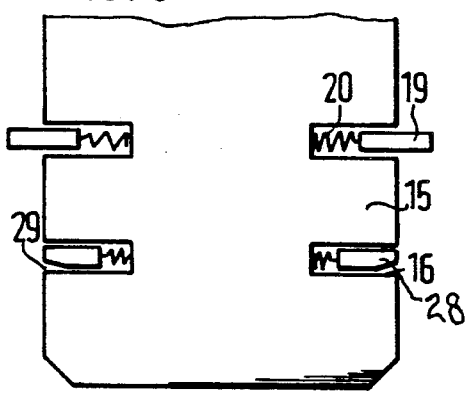
FIG. 6 shows a gripping mechanism for the object of FIG. 5.

The drilling device illustrated in FIG. 1, which is also used to obtain unadulterated water samples, is generally indicated by reference numeral 1 and drills a bore 2. A circular gap remains between a bore wall 3 and a boring bar 4. This results from the difference between the diameters of a drilling tool 5 and the boring bar 4. The drilling tool 5 is positioned directly beneath a perforated bar conduit 6.

Perforations 7 of the bar conduit 6 are arranged in a large number of horizontal and vertical rows and penetrate the tube casing in a more or less radial direction. A largely ring-shaped body of filter sand 8 fills the circular space between the perforated bar conduit 6 and the bore wall 3 and reaches to the bottom of the bore 2. It extends to the last nonperforated conduit 9 of the boring bar 4.

According to the embodiment illustrated in FIGS. 5 through 8, a perforated insert 10 is positioned inside the perforated bar conduit 6 which restrains the filter sand, permitting only filter-sand-free water to enter the boring bar 4 when a pump, not illustrated, pumps the water to the surface.

The perforated insert 10 and the perforated bar conduit 6 are joined via locking bolts 11 and a bracket 12, thereby making sure that the perforated insert 10 fits tightly in the perforated bar conduit 6. Openings 13 are cut into the perforated insert 10; according to the example illustrated in FIG. 5, these openings are longitudinal slots of approximately 0.5 mm in width, thereby effectively restraining the coarse filter sand in the filter sand body 8.

A gripping mechanism 15 is shown in the transitional area 14 between the perforated bar conduit 6 and the nonperforated bar conduit 9. This gripping mechanism 15 is used to remove the perforated insert 10 in order to replace it with a nonperforated insert 30 shown in the other figures when drilling is begun.

The gripping mechanism 15 has draw-in bolts 16 which click into cutouts 17 in an inner wall 18 of the perforated insert 10. The gripping mechanism 15 via the draw-in bolts 16 is able to remove the entire perforated insert 10 through the boring bar 4. Recessed bolts 19 are attached to the upper end and, like the draw-in bolts 16, are spring-loaded, shown at 20, so that they can move toward the perforated insert 10, thereby allowing the bolts to precisely guide or precisely grip the insert. The functions of the recessed bolts 19 will be further explained with reference to FIG. 7.

A locking mechanism 22 is fitted to the lower end of the perforated insert 10 which allows the water to be tested to flow into the bar interior 23, intentionally circumventing the filter sand body. The locking mechanism 22 acts as a nonreturn valve.

FIG. 6 shows a gripping mechanism 15 with spring-loaded draw-in bolts 16 and recessed bolts 19 which project from the corresponding holes or cutouts, unless they are blocked by the inner wall 18 of the perforated insert 10 or the nonperforated insert 30. The lowest side 28 of at least the draw-in bolts 16 facing the bore are bevelled at 29, thereby permitting the gripping mechanism 15 to engage with the perforated insert 10 or the nonperforated insert 30 by first drawing back from and then clicking into the appropriate cutout 17 in the inner wall 18 of the perforated insert 10 or the nonperforated insert 30, once this is required.

Figure 7:
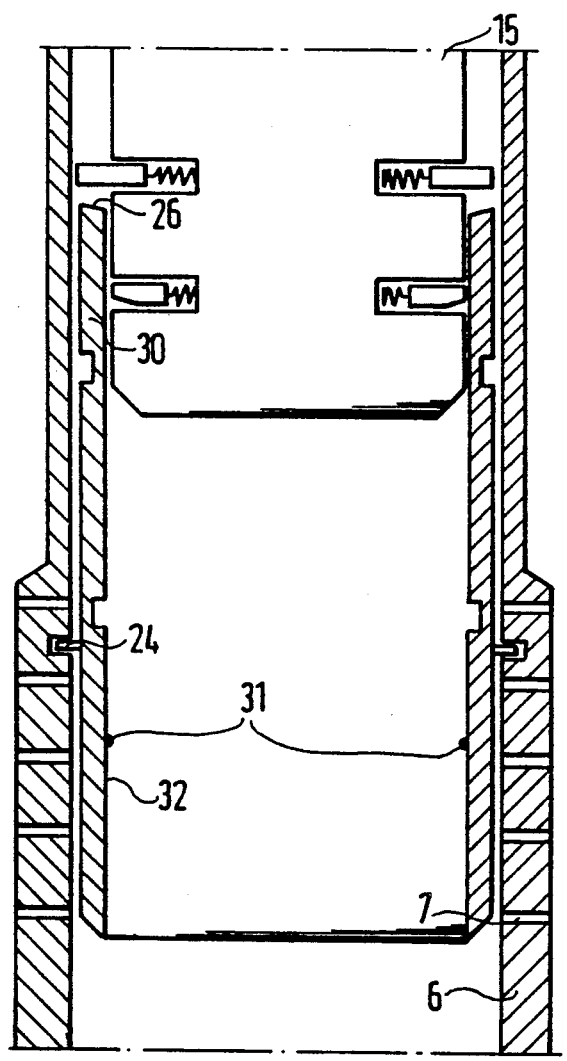
FIG. 7 shows the gripping mechanism positioned in the boring bar according to FIG. 2.

FIG. 7 shows the lower region of the boring bar 4, with the nonperforated insert 30 being inserted into the region of the perforated bar conduit 6 immediately above the gripping mechanism 15. The nonperforated insert 30 is then used to close the perforations 7 in the perforated bar conduit 6. When spherical bolts 24 provided on the nonperforated insert 30 have clicked into a groove 12 in the inner wall 18 of the perforated bar conduit 6, the nonperforated insert 30 has reached its designated position. To ensure the nonperforated insert 30 is properly seated, the gripping mechanism 15 presses down onto an insert edge 26 via the recessed bolts 19, as shown. This always places the nonperforated insert 30 in its required final position.

In order to subsequently retrieve the nonperforated insert 30 illustrated in FIG. 8, the gripping mechanism 15 is lowered into the insert with the recessed bolts 19 withdrawn or in the process of being withdrawn. Once the draw-in bolts 16 click into the groove 25, the recessed bolts 19 are out of operation. The gripping mechanism 15 can be retrieved, taking the nonperforated insert 30 with it.

If the gripping mechanism 15 is inserted too far into the nonperforated insert 30, it will be blocked by a limit element 31 on an inner wall 32 of the nonperforated insert 30.

Figure 8:
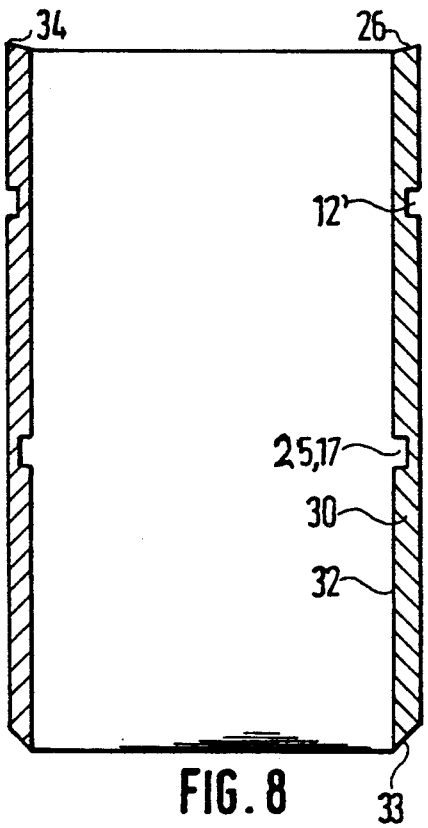
FIG. 8 shows a nonperforated insert according to the invention for the embodiment according to FIGS. 1 through 3.

Edges 33 and 34 of the nonperforated insert 30 are beveled, as shown in FIGS. 7 and 8. For practical purposes, the beveled sections are formed in the opposite direction when working with a device in which the nonperforated inserts 30 are fixed in the region of the nonperforated conduit 9 lying above it during water sampling. In this embodiment, the nonperforated inserts 30 or the perforated inserts 10 do not need to be retrieved, and both the perforated insert 10 and the perforated bar conduit 6 form a single unit.

In the embodiment of FIG. 2, the upper end of the perforated bar conduit 6 is attached to the adjacent nonperforated conduit 9 at the point indicated by reference numeral 35. A snap ring 36 is used to hold a filter tube 37, which should be made of plastic, in the perforated bar conduit 6. The filter tube 37 is supported by a bundle of rings 38 on the inside of the perforated bar conduit 6. Its inner diameter is equivalent to the inner diameter of the hollow bar. The advantage of the described arrangement lies in the fact that perforations 40 in the perforated bar conduit 6, which weaken the conduit casing 39, require only a small number of free openings, which will not excessively weaken the conduit. On the other hand, the narrow slots in the filter tube 37 needed for the filter edge have a relatively large open area and a relatively low stability; however, joining the insert to the perforated conduit increases this stability, making it possible to absorb any forces which may occur.

FIG. 2 shows the inserted nonperforated insert 30 with O-ring seals 42 and 41 fitted to its upper and lower end, respectively. This ensures that the bore rinse cannot pass through the perforations 40 in the perforated bar conduit 6 as long as the drill is in operation.

FIG. 3, on the other hand, shows the inserted perforated insert 10, which also has O-ring seals 43 and 44 at its upper and lower ends, respectively. In this example, perforations 45 are equal to the size and free area of the filter sand.

As indicated in FIG. 4, the inserted nonperforated insert 30 allows a nonreturn valve 46 to be opened by loading a valve spring 47 as soon as the bore rinse presses the boring bar against the valve body 46.

It will be understood by those skilled in the art to which this invention appertains that various changes and modifications may be made to the invention as described without departing from the scope of the appended claims.

What is claimed is:

1. A method for producing an unadulterated water sample when drilling a well using a hollow boring bar for transferring a drilling fluid to a drilling tool, said hollow boring bar comprising at least one nonperforated bar section and a perforated bar section disposed between said at least one nonperforated bar section and said drilling tool, said method comprising the steps of:

inserting a nonperforated insert in said perforated bar section through said at least one nonperforated bar section;

drilling a bore to at least a first water conducting horizontal with said drilling tool, said bore having a diameter greater than said hollow boring bar;

filling the space between said hollow boring bar and the walls of said bore with a filter sand to a depth greater than the length of said perforated bar section;

removing said nonperforated insert from said hollow boring bar permitting water from at least a first water conducting horizontal to enter said perforated bar section; and pumping a water sample from within said perforated bar section at said at least first water conducting horizontal.

2. The method of claim 1 further including the step of inserting a perforated insert into said perforated bar section after the step of removing said nonperforated insert.

3. The method of claim 2 further including the steps of:

removing said perforated insert and reinserting said nonperforated insert adjacent to said perforated bar section;

drilling a bore to at least a second water conducting horizontal with said drilling tool;

filling the space between said hollow boring bar and the walls of said bore with a filter sand to a depth greater than the length of said perforated bar section;

removing said nonperforated insert from said hollow boring bar and inserting said perforated insert in its place; and pumping a second water sample from within said perforated bar section at said second water conducting horizontal.

4. A device for drilling a well and for producing unadulterated water samples comprising:

a drilling tool;

a hollow boring bar having one end attached to said drilling tool, said hollow boring bar adapted to transfer a drilling fluid to said drilling tool, said hollow boring bar having a perforated section adjacent said one end;

a nonperforated insert slidably insertable into said hollow boring bar adjacent to said perforated section to prevent water from a water conducting horizontal from passing through said perforated section into said hollow boring bar;

a perforated insert slidably insertable into said hollow boring bar adjacent to said perforated section to permit said unadulterated water sample to enter said hollow boring bar; and wherein said nonperforated insert is inserted into said perforated section of said hollow boring bar during the drilling of said well and said perforated insert is inserted in said perforated section of said hollow boring bar to sample the water in said water conducting horizontal.

5. The device of claim 4 further comprising gripper means for inserting and removing said perforated and nonperforated inserts from said hollow boring bar.

6. The device of claim 4 wherein said perforated section has a locking mechanism disposed at an end adjacent to said drilling tool which is closed when said perforated insert is inserted therein.

7. The device of claim 5 wherein said locking mechanism is a nonreturn valve which is resiliently biased against an end of said perforated insert.

8. The device of claim 4 wherein said perforated section has a filter tube inserted therein to restrain a filter sand from passing through said perforated section.

9. The device of claim 5 wherein said perforated and nonperforated inserts have projecting locking bolts which engage an annular groove provided in the internal surface of said perforated section to hold said perforated and nonperforated inserts in said perforated section.

10. The device of claim 5 wherein said perforated and nonperforated inserts have annular cutouts provided in their internal surfaces, said gripper means comprises at least one draw-in bolt receivable in said annular cutouts to lock said gripper means to said perforated and nonperforated inserts permitting said perforated and nonperforated inserts to be removed from said hollow boring bar.

11. The device of claim 9 wherein said locking bolts are spring loaded spherical bolts.

12. The device of claim 10 wherein said gripper means has at least one spring loaded recess bolt which engages the end of said perforated and nonperforated inserts opposite said drilling tool.

13. The device of claim 10 wherein the ends of said at least one draw-in bolts facing said drilling tool are beveled.

14. The device of claim 5 wherein each of said perforated and nonperforated inserts have limiting elements which project from their respective internal surfaces which limit the distance said gripper means may be inserted into said perforated and nonperforated inserts, respectively.

15. The device of claim 8 wherein said perforated section has a plurality of circular openings, each circular opening having an opening cross section of 8 to 30 millimeters and wherein said filter tube has openings and each opening of said filter tube have an opening cross section of 0.5 millimeters.

16. The device of claim 15 wherein said filter tube comprises a plurality of supports with a width of approximately 0.5 millimeters.

17. The device of claim 4 wherein said perforated and nonperforated inserts are connected to each other and are movable as a single unit.

* * * * *

UNITED STATES PATENT AND TRADEMARK OFFICE
CERTIFICATE OF CORRECTION

PATENT NO. : 5,097,914
DATED : March 24, 1992
INVENTOR(S) : Gerhard Grotendorst

It is certified that error appears in the above-identified patent and that said Letters Patent is hereby corrected as shown below:

Column 3, line 26, before "12" insert ---- or groove ----.

Column 4, line 7, delete "a" and insert ---- the ----.

Col. 5, line 28, after "from" insert ---- said ----.

Column 6, line 20, delete "5" and insert ---- 6 ----.

Column 6, line 47, delete "bolts" and insert ---- bolt ----.

Column 6, line 59, delete "have" and insert ---- has ----.

Signed and Sealed this

Third Day of August, 1993

Attest:

MICHAEL K. KIRK

Attesting Officer     Acting Commissioner of Patents and Trademarks